United States Patent
Yonce et al.

(10) Patent No.: US 6,819,953 B2
(45) Date of Patent: Nov. 16, 2004

(54) SYSTEM AND METHOD FOR DETECTION OF PACING PULSES WITHIN ECG SIGNALS

(75) Inventors: David J. Yonce, Fridley, MN (US); Peter John Ormsby, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 22 days.

(21) Appl. No.: 10/251,310

(22) Filed: Sep. 19, 2002

(65) Prior Publication Data

US 2003/0023176 A1 Jan. 30, 2003

Related U.S. Application Data

(62) Division of application No. 09/516,533, filed on Mar. 1, 2000, now Pat. No. 6,447,404.

(51) Int. Cl.[7] .................................. A61B 5/04
(52) U.S. Cl. ....................................... 600/510
(58) Field of Search ................. 600/509, 510, 600/523

(56) References Cited

U.S. PATENT DOCUMENTS

| | | | |
|---|---|---|---|
| 3,643,168 A | 2/1972 | Manicki .................... 325/459 |
| 3,723,926 A | 3/1973 | Thomas et al. ............. 335/268 |
| 3,742,938 A | 7/1973 | Stern ........................ 128/2.05 |
| 3,777,570 A | 12/1973 | Thomas et al. ............... 73/398 |
| 3,826,143 A | 7/1974 | Thomas et al. ........... 73/398 C |
| 3,828,227 A | 8/1974 | Millard et al. ............... 317/230 |
| 3,859,574 A | 1/1975 | Brazier ...................... 317/230 |
| 3,938,228 A | 2/1976 | Kemkers et al. ........... 29/25.42 |
| 4,047,790 A | 9/1977 | Carino ...................... 339/220 |
| 4,086,148 A | 4/1978 | Badia ......................... 204/33 |
| 4,088,108 A | 5/1978 | Hager ................. 123/148 CG |
| 4,131,935 A | 12/1978 | Clement .................... 361/433 |
| 4,539,999 A | 9/1985 | Mans ......................... 128/696 |
| 4,571,662 A | 2/1986 | Conquest et al. ........... 361/306 |
| 4,664,116 A | 5/1987 | Shaya et al. ................ 128/419 |
| 4,782,340 A | 11/1988 | Czubatyj et al. ....... 340/825.83 |
| 4,796,638 A | 1/1989 | Sasaki ....................... 128/696 |
| 5,131,388 A | 7/1992 | Pless et al. ............. 128/419 D |
| 5,439,760 A | 8/1995 | Howard et al. ............... 429/94 |
| 5,448,997 A | 9/1995 | Kruse et al. ................ 128/697 |
| 5,471,087 A | 11/1995 | Buerger, Jr. ................ 257/532 |
| 5,507,966 A | 4/1996 | Liu ........................... 252/62.2 |
| 5,522,851 A | 6/1996 | Fayram ........................ 607/5 |
| 5,527,346 A | 6/1996 | Kroll ............................ 607/5 |
| 5,554,178 A | 9/1996 | Dahl et al. .................. 607/122 |
| 5,584,890 A | 12/1996 | MacFarlane et al. ....... 29/25.03 |
| 5,628,801 A | 5/1997 | MacFarlane et al. ....... 29/25.03 |
| 5,658,319 A | 8/1997 | Kroll ............................ 607/7 |
| 5,660,737 A | 8/1997 | Elias et al. .................... 216/6 |
| 5,716,729 A | 2/1998 | Sunderland et al. .......... 429/66 |
| 5,738,104 A | 4/1998 | Lo et al. ..................... 128/706 |
| 5,754,394 A | 5/1998 | Evans et al. ................ 361/516 |
| 5,779,699 A | 7/1998 | Lipson ........................ 606/41 |
| 5,779,891 A | 7/1998 | Andelman ............... 210/198.2 |
| 5,800,724 A | 9/1998 | Habeger et al. ............... 216/35 |

(List continued on next page.)

FOREIGN PATENT DOCUMENTS

| | | | |
|---|---|---|---|
| WO | WO-98/27562 | 6/1998 | ........... H01G/4/18 |
| WO | WO-99/51302 | 10/1999 | .......... A61N/1/375 |
| WO | WO-00/19470 | 4/2000 | .......... H01G/9/055 |

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

A system and method for detecting pacing pulses generated by a cardiac pacemaker within an ECG signal. The method involves decomposing the ECG signal into high and low-frequency components that represent the energy of the input signal in high and low-frequency bands. The timing of energy pulses detected within the high and low-frequency bands are then used to determine whether the pulses may represent a pacing pulse.

20 Claims, 3 Drawing Sheets

U.S. PATENT DOCUMENTS

| | | | | |
|---|---|---|---|---|
| 5,801,917 | A | 9/1998 | Elias | 361/535 |
| 5,814,082 | A | 9/1998 | Fayram et al. | 607/5 |
| 5,867,363 | A | 2/1999 | Tsai et al. | 361/502 |
| 5,908,151 | A | 6/1999 | Elias | 228/110.1 |
| 5,922,215 | A | 7/1999 | Pless et al. | 216/6 |
| 5,926,357 | A | 7/1999 | Elias et al. | 361/302 |
| 5,930,109 | A | 7/1999 | Fishler | 361/508 |
| 5,963,418 | A | 10/1999 | Greenwood, Jr. et al. | 361/508 |
| 5,968,210 | A | 10/1999 | Strange et al. | 29/25.03 |
| 5,973,906 | A | 10/1999 | Stevenson et al. | 361/302 |
| 5,983,472 | A | 11/1999 | Fayram et al. | 29/25.42 |
| 6,002,969 | A | 12/1999 | Machek et al. | 607/122 |
| 6,006,133 | A | 12/1999 | Lessar et al. | 607/5 |
| 6,009,348 | A | 12/1999 | Rorvick et al. | 607/5 |
| 6,032,075 | A | 2/2000 | Pignato et al. | 607/5 |
| 6,040,082 | A | 3/2000 | Haas et al. | 429/163 |
| 6,042,624 | A | 3/2000 | Breyen et al. | 29/25.03 |
| 6,110,233 | A | 3/2000 | O'Phelan et al. | 29/25.03 |
| 6,052,625 | A | 4/2000 | Marshall | 607/122 |
| 6,094,788 | A | 8/2000 | Farahmandi et al. | 25/24.41 |
| 6,099,600 | A | 8/2000 | Yan et al. | 29/25.03 |
| 6,104,961 | A | 8/2000 | Conger et al. | 607/122 |
| 6,118,651 | A | 9/2000 | Mehrotra et al. | 361/509 |
| 6,141,205 | A | 10/2000 | Nutzman et al. | 361/509 |
| 6,157,531 | A | 12/2000 | Breyen et al. | 361/519 |
| 6,184,160 | B1 | 2/2001 | Yan et al. | 438/800 |
| 6,191,931 | B1 | 2/2001 | Paspa et al. | 361/302 |
| 6,212,063 | B1 | 4/2001 | Johnson et al. | 361/517 |
| 6,249,423 | B1 | 6/2001 | O'Phelan et al. | 361/502 |
| 6,249,709 | B1 | 6/2001 | Conger et al. | 607/122 |
| 6,256,542 | B1 | 7/2001 | Marshall et al. | 607/126 |
| 6,259,954 | B1 | 7/2001 | Conger et al. | 607/122 |
| 6,275,729 | B1 | 8/2001 | O'Phelan et al. | 607/5 |
| 6,297,943 | B1 | 10/2001 | Carson | 361/500 |
| 6,299,752 | B1 | 10/2001 | Strange et al. | 205/152 |
| 6,321,114 | B1 | 11/2001 | Nutzman et al. | 607/5 |
| 6,326,587 | B1 | 12/2001 | Cardineau et al. | 219/121.68 |
| 6,388,866 | B1 | 5/2002 | Rorvick et al. | 361/503 |
| 6,402,793 | B1 | 6/2002 | Miltich et al. | 29/25.03 |
| 6,442,015 | B1 | 8/2002 | Niiori et al. | 361/502 |
| 6,477,037 | B1 | 11/2002 | Nielsen et al. | 361/520 |
| 6,477,404 | B1 | 11/2002 | Yonce et al. | 600/510 |
| 6,493,212 | B1 | 12/2002 | Clarke et al. | 361/521 |

SYSTEM AND METHOD FOR DETECTION OF PACING PULSES WITHIN ECG SIGNALS

CROSS-REFERENCE TO RELATED APPLICATION(S)

This application is a division of U.S. application Ser. No. 09/516,533, filed on Mar. 1, 2000, the specification of which is incorporated by reference herein.

FIELD OF THE INVENTION

This invention pertains to systems and methods for detecting pulses within electrical signals and, in particular, within surface electrocardiograms.

BACKGROUND

Implanted pacemakers generate pacing pulses in order to stimulate the heart to beat in the absence of spontaneous beats. Such devices, which may be either dedicated pacemakers or other devices with a pacing functionality (e.g., implantable cardioverter/defibrillators), thus produce detectable electrical signals when the heart is paced. Signals from implanted pacemakers often couple to the body surface and hence are present in electrocardiograms (ECGs). Pacing pulses in electrocardiograms are detected for two purposes: one, to provide the clinician with a marker showing pacemaker activity and, two, so that the visible pacemaker artifacts can be removed from the ECG waveforms. Prior designs for doing this involve filtering the incoming ECG data to a specific high frequency band (1–15 KHz) and then comparing the energy in the band to a threshold level. Refinements to this idea include variable sensing thresholds to help reject noise, and higher frequency filtering to attempt edge detection. Edge detection by high frequency filtering, however, is extremely susceptible to broadband noise from both telemetry and minute ventilation signals.

SUMMARY OF THE INVENTION

It is a primary object of the present invention to provide a system and method for detecting pacing pulses within ECG data. Pacing pulses have significant high-frequency energy due to the sharp transitions at the rising and falling edges of the pulse. A pacing pulse also has a significant amount of low-frequency energy that occurs in a particular time relation to the occurrence of the high-frequency energy. In accordance with the invention, an ECG signal is processed to determine its energy content in both high and low frequency bands. If such energy is present above a threshold amount in each band, and meets specified timing criteria, a pacing pulse is detected.

A system for detecting pacing pulses within an ECG input signal in accordance with the invention includes high-frequency and low-frequency bandpass filters for filtering the input signal into high-frequency and low-frequency components that represent the energy of the input signal within the respective frequency bands. Exemplary high and low-frequency bandpass filters would have center frequencies of approximately 1 KHz and 30 KHz. The system also includes pulse detection circuitry for detecting high-frequency and low-frequency energy pulses within the high and low-frequency components, respectively, and at least one timer for measuring one or more time intervals between detections of energy pulses. Logic circuitry is provided for detecting a pacing pulse within the input signal if the detections of the high and low-frequency energy pulses meet specified timing criteria. The timing criteria may then dictate that a pacing pulse is detected only if detection of a low-frequency energy pulse occurs within a specified time interval with respect to detection of a high-frequency energy pulse. In one embodiment, the logic circuitry detects possible rising and falling edges of a pacing pulse when first and second high-frequency energy pulses are detected by the pulse detection circuitry. The timing criteria for detection of a pacing pulse may then include detection of the second high-frequency energy pulse within a specified minimum time interval from the detection of the first high-frequency energy pulse. The timing criteria may further include detection of the second high-frequency energy pulse within a specified maximum time interval from detection of the first high-frequency energy pulse.

In order to distinguish sensed energy pulses from noise, the pulse detection circuitry detects energy pulses by comparing sensed energy pulses to a threshold value. In one embodiment, the pulse detection circuitry detects energy pulses in the high-frequency band by comparing a sensed pulse to a threshold value derived from a sensed RMS level in the input signal. In this manner, a dynamic noise floor is established. In another embodiment, the pulse detection circuitry detects energy pulses in the high-frequency band by comparing a sensed pulse to a threshold value based upon a prior detection of a high-frequency energy pulse. The threshold value based upon a prior detection of a high-frequency energy pulse may then be updated by the logic circuitry when a pacing pulse is detected. Particular embodiments of the pulse detection circuitry may combine threshold testing such that energy pulses are detected only if a sensed pulse exceeds thresholds based upon a sensed RMS level, a prior pulse detection, and a fixed value.

DETAILED DESCRIPTION OF THE INVENTION

The present invention may be practiced in a number of different environments, but is particularly suitable for use in an external programmer used to program and receive data from implantable cardiac pacemakers. Such a programmer incorporating a system in accordance with the invention provides the clinician with a more informative ECG display, by showing either the isolated pacing pulses generated by the pacemaker or the ECG signal with the pacing pulses removed. Other embodiments may present the user with a display on a screen to indicate pacing pulse width in numerical format, or with a pacing indicator included within the ECG data that changes color with pacing width. Any of these or other possible data displays, however, depends upon being able to separate pacing pulses from the intrinsic signals generated by the heart in ECG data.

In accordance with the present invention, pacing pulses are detected within ECG signals by filtering the signal in both high and low frequency bands and then looking for threshold energies in those bands. Detecting pulses in this manner obtains greater sensitivity and noise rejection than previous detection methods. The embodiment to be described utilizes a dual-band detection method using bandpass filters with center frequencies of approximately 1 KHz and 30 KHz. The energies in both bands are then compared with one or more thresholds to indicate a possible pacing pulse. A pacing pulse is made up of positive and negative going edges that have significant energy in the high frequency band. In order for a pacing pulse to be detected and considered valid, the two edges of the pulse must therefore be detected in the 30 KHz range. In addition, low frequency energy must also be detected during the same time window as the two edges. This allows rejection of noise that is present in only one of the bands, such as telemetry interference present in the 30 KHz band. In another aspect of the invention, the two detected edges must occur within a specified maximum time interval and, further must occur with a specified time interval of each other. In the embodiment to be described below, the two edges in the 30 KHz range must occur within 100 microseconds and within 2 milliseconds of each other. This allows rejection of broadband pulses that occur less frequently than 2 milliseconds, such as minute ventilation signals. These detection conditions provide improved noise rejection compared with earlier designs and yet also allow detection of pacing signals that were previously too small for detection. The method also allows rejection of signals of greater amplitude than the pacing pulses while still providing the detector with an increased sensitivity.

Figure 1:
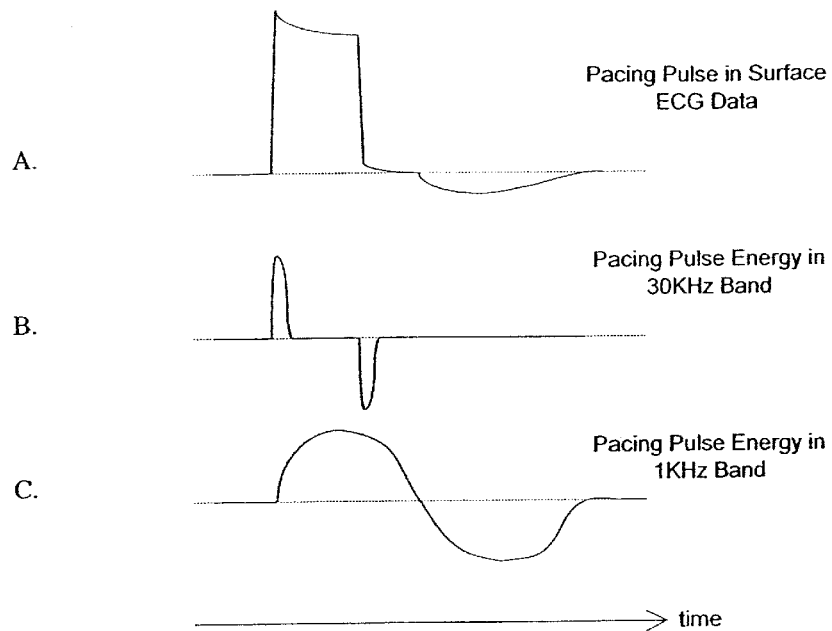
FIG. 1 shows an ECG waveform and the detected pulse energies in the 1 KHz and 30 KHz frequency bands.

In the graph labeled A in FIG. 1, there is show a waveform made up of an ECG signal that also contains a pacing pulse. The graphs labeled B and C show the frequency content of a pacing pulse in the 30 KHz and 1 KHz bands, respectively. The pacing pulse frequency content in the 30 KHz band peaks during the edge transitions of the pacing pulse, while the 1 KHz band exhibits a wide peak between and after the pacing edges. A pace is detected in accordance with the invention by detecting threshold energies in both bands and within specified time intervals. In a presently preferred embodiment, a pulse is considered valid if the detection circuitry detects two distinct edges within 0.1 to 2 ms of each other, and low-frequency energy between or immediately following the edges. This scheme rejects noise that occurs in only one of the two bands of interest (telemetry noise occurring in the 30 KHz band, for instance), but filtered from the 1 KHz band. The system also rejects noise bursts (such as minute ventilation signals), that occur less frequently than once every 2 ms.

Figure 2:
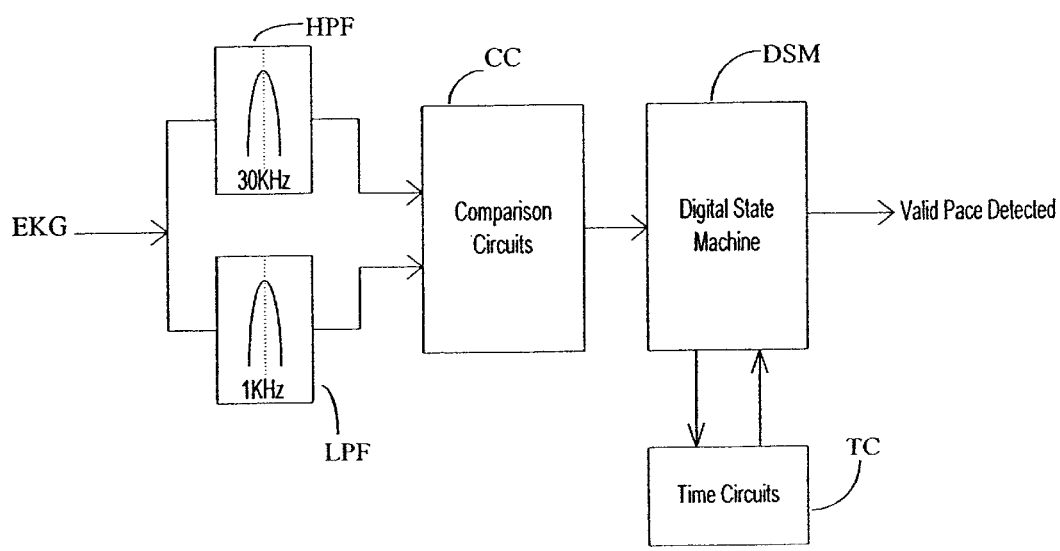
FIG. 2 is a block diagram of a system in accordance with the invention.

FIG. 2 is a block diagram of the pace detection system in one embodiment. An ECG signal, possibly containing a pacing pulse, is separated into its high and low frequency components by high-frequency bandpass filter HPF and low-frequency bandpass filter LPF, respectively. The outputs of the filters are then input to comparison circuits CC that determine if the energies detected in the two bands are present at the and at sufficient magnitudes. A digital state machine DSM makes up the logic circuitry that performs the detection algorithm based upon energy comparisons performed in the analog filtering and threshold detection hardware and in accordance with lapsed time intervals provided by the timing circuits TC. The state machine thus controls the pace detect functionality and also tailors the detection criteria to the morphology of the pacing pulses. If a pacing pulse is detected, the signal labeled Valid Pace Detected is asserted. Instead of using analog filters and comparison circuitry, an alternative embodiment uses digital techniques for filtering samples of the sensed waveform and performing the threshold detections on the digitized filter outputs. Because the detection algorithm searches for high-frequency components, however, complete implementation in the digital domain requires fast data sampling and a powerful DSP (digital signal processor).

Figure 3:
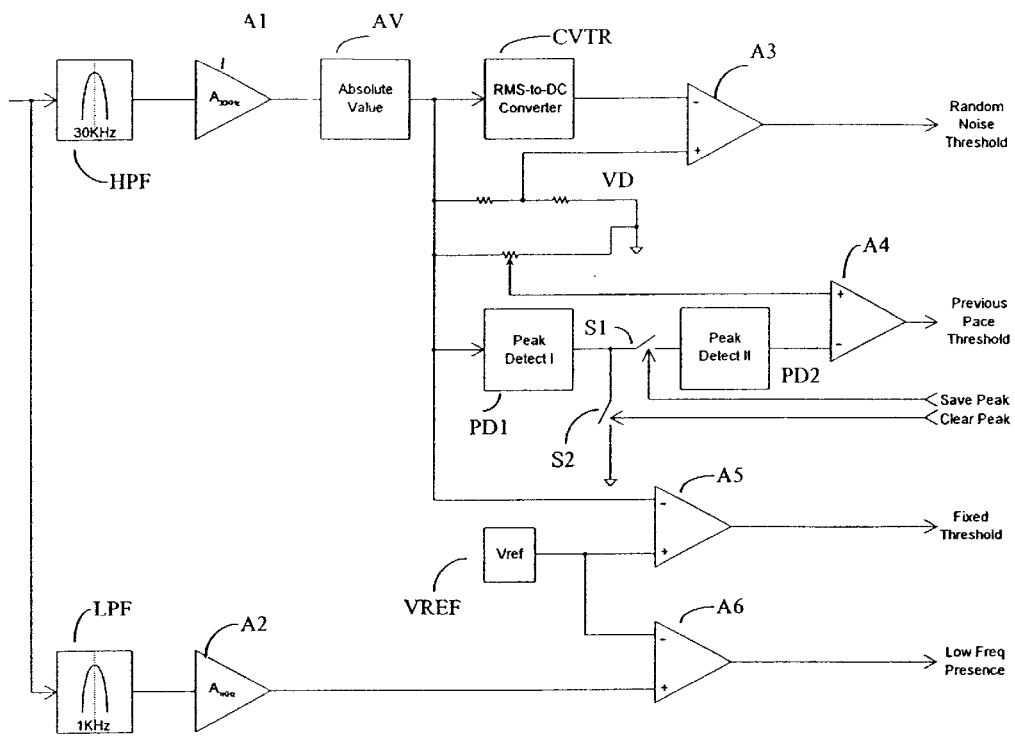
FIG. 3 is a schematic of the pulse detection circuitry.

FIG. 3 is a schematic of the bandpass filters and pulse detection circuitry that comprise the analog input stages in this embodiment. In order for a high-frequency energy pulse to be considered as a valid pacing pulse edge, it must be above a fixed minimum noise level and also above a dynamic noise floor established by an RMS-to-DC converter CVTR and a peak detection circuit. Using these measurement techniques to produce the threshold allows a greater immunity against a wider variety of noise. The RMS measurement from converter CVTR provides a threshold floor in the case of a continuous noise source with a relatively low crest factor. An RMS detector responds poorly, however, to pulsed noise sources, such as power-line spikes. The peak detection circuitry, comprising peak detectors PD1 and PD2 together with a comparator A4, accounts for this and keeps a measure of the previous peaks, decaying with a time constant of 0.8 seconds in this embodiment. The peak detector measurement is actually a sample-and-hold system made up of the two peak detectors PD1 and PD2. This allows incoming signals to not disturb the peak detector threshold until after the voltage comparisons are completed. As an example, peak detector PD1 will follow the rising edge of an incoming signal until it begins to decay back to the baseline. Peak detector PD2, however, remains unchanged, allowing the circuitry to determine if the incoming signal is part of a pair of peaks (i.e., representing the rising and falling edges of a pace pulse). Once the system recognizes a valid pace, the voltage capacitively stored at peak detector PD1 is transferred to peak detector PD2 by closure of switch S1, which updates the peak detection threshold. If a rising edge is detected by the system but rejected as noise, the system resets peak detector PD1 by closure of switch S2 and leaves peak detector PD2 unchanged.

Still referring to FIG. 3, the input ECG signal is split and fed separately to the high-frequency and low-freqency bandpass filters HPF and LPF. The low-frequency energy from filter LPF is buffered by amplifier A2 and then tested to determine if it exceeds the fixed threshold as defined by a voltage reference VREF by comparator A6. If so, the signal Low Freq Presence is asserted indicating that threshold energy has been detected in the low-frequency band. The high-frequency energy from filter HPF is buffered by amplifier A1, rectified by rectifier AV to result in the absolute value of the signal, and then passed to three separate threshold detectors. Comparator A5 performs the same threshold test on the high-frequency energy signal as does comparator A6 on the low-frequency signal, using VREF as the fixed threshold. If the detected high-frequency energy exceeds the fixed threshold, the Fixed Threshold signal is asserted. Comparator A3 performs a threshold test of a fraction of the high-frequency energy, as determined by voltage divider VD, with respect to the output of the RMS-to-DC Converter CVTR. As described above, this is the dynamic noise floor and, if it is exceeded, the signal Random Noise Threshold is asserted by the comparator. Comparator A4 then tests whether the filtered input signal exceeds the previously stored peak in peak detector PD2. If so, the signal Previous Pace Threshold is asserted.

Figure 4:
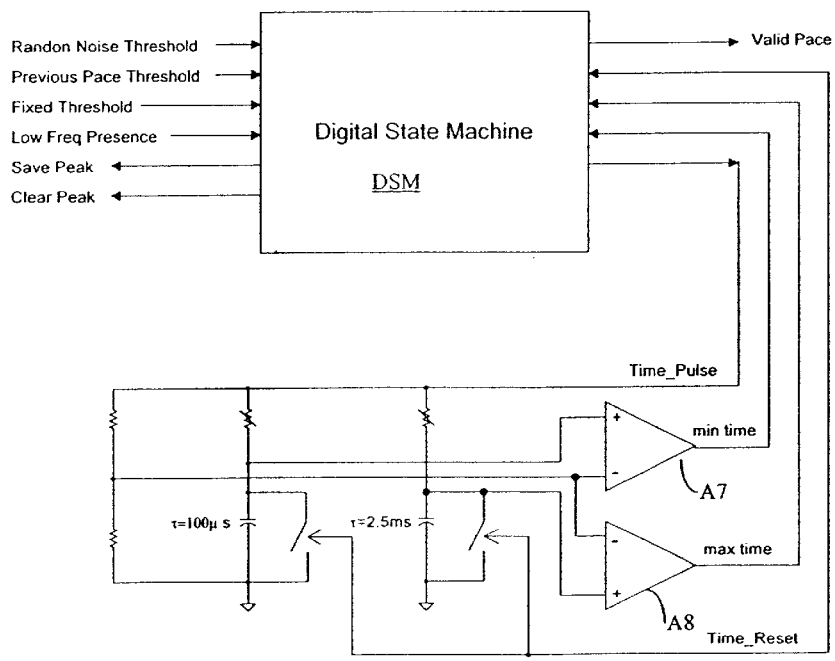
FIG. 4 shows an exemplary timing circuit used by the digital state machine.

The tests performed by the pulse detection circuitry are processed by logic circuitry in order to detect a pacing pulse. In this embodiment, the logic circuitry is a dedicated digital or sequential state machine DSM as depicted in FIG. 4. Such a state machine may be implemented, for example, as discrete logic components, in a field-programmable gate array (FPGA), or as software instructions executed by a processor. In the particular embodiment described here, the state machine is implemented as an FPGA which is driven by a 4.9152 MHz clock. This causes the threshold comparison signals to be sampled, and the state machine updated, once every 203 ns. The state machine receives the comparator output signals generated by the threshold detection circuitry as described above, and asserts the Clear Peak and Save Peak signals to close switches S2 and S1, respectively, to reset the peak detectors. In processing the threshold detection signals, the state machine requires timing information to define the maximum and minimum time intervals used to determine whether detected edges represent a pacing pulse in accordance with the present method. This timing function can be performed digitally or by analog RC timers. Analog RC timers are employed in the presently described embodiment as depicted in FIG. 4. Two timers are used in this embodiment, one for the maximum-time and the other for the minimum time. The timers are made up of amplifiers A7 and A8, and resistor-capacitor networks with differing time constants, exemplary constants being shown in the figure. The Time_Pulse signal asserted by the state machine charges the capacitors and starts the timers. Discharge of the capacitors causes assertion of the timeout signals by comparators A7 and A8, MinTime in the case of the minimum-timer and MaxTime in the case of the maximum-timer. Both timers are reset by the state machine asserting the Time_Reset signal which closes switches to discharge the capacitors.

Figure 5:
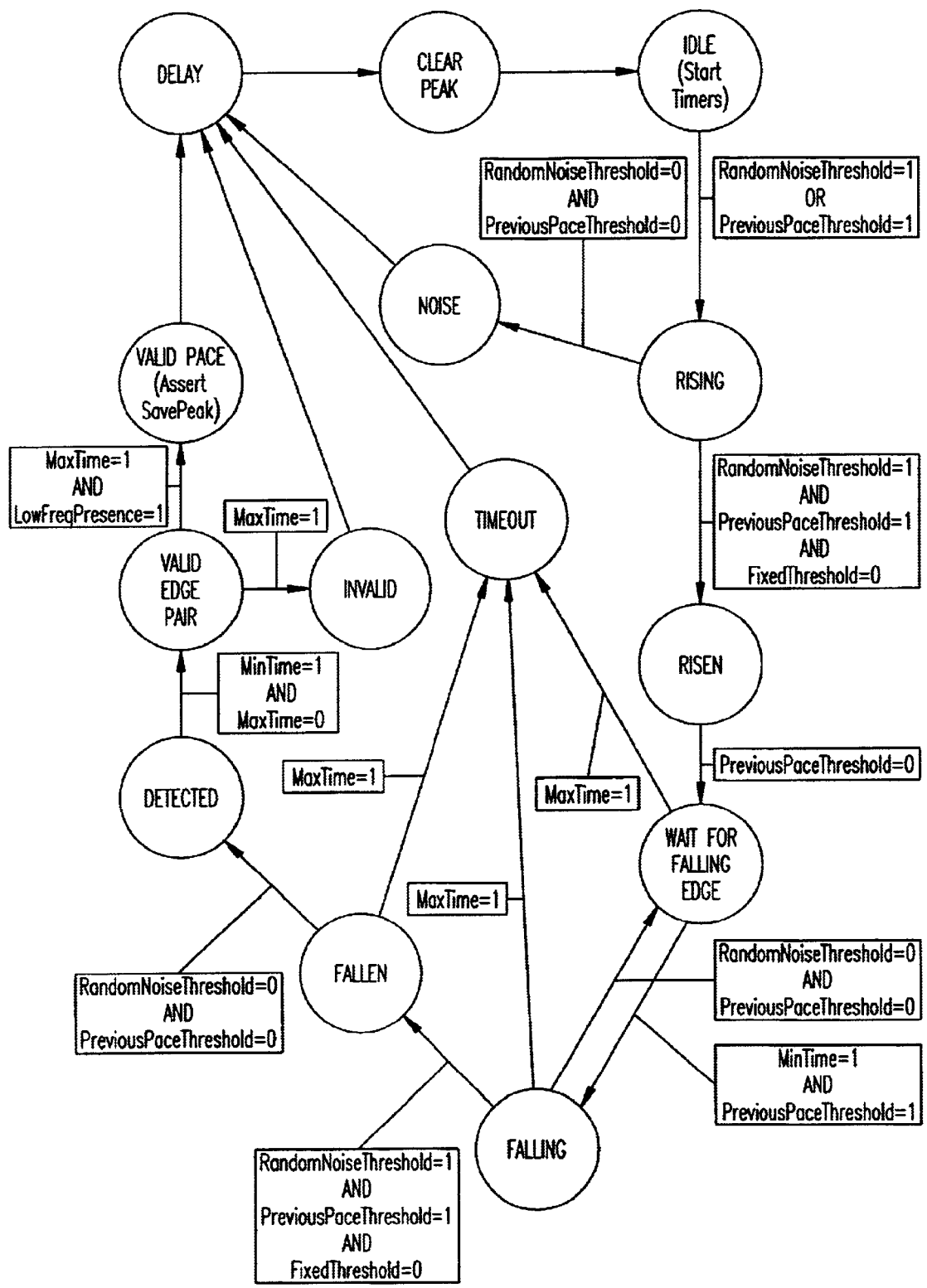
FIG. 5 is a state diagram illustrating the operation of the digital state machine.

FIG. 5 illustrates the operation of the state machine DSM in detail. The machine starts in an IDLE state where it waits for comparison signals from the comparison circuits. From the IDLE state, the machine transitions to the RISING state and starts the two RC timers after receipt of an asserted Random Noise Threshold or Previous Pace Threshold signal, indicating that the high-frequency filtered input signal has exceeded at least one of those thresholds and may be due to the rising edge of a pacing pulse. The machine stays in the RISING state until the high-frequency filtered input signal has exceeded the noise, previous pace, and fixed thresholds as indicated by the assertion of the Random Noise Threshold, Previous Pace Threshold, and Fixed Threshold signals by the comparison circuit. (Note that assertion of the noise and previous pace thresholds is a logical 1, while assertion of the Fixed Threshold signal is a logical 0 due to the polarity of the comparators A5 and A6.) A transition is then made to the RISEN state. If the Random Noise Threshold and Previous Pace Threshold signals are deasserted before that condition is reached, however, the signal is regarded as noise. The machine then transitions to the NOISE state and thence to the DELAY state and back to the IDLE state. (After a predetermined time interval, the machine transitions to the CLEAR PEAK state where the peak value stored in peak detector PD1 is cleared by asserting the Clear Peak signal before moving back to the IDLE state.) From the RISEN state, the machine transitions to the WAIT FOR FALLING EDGE state once the input signal has decayed below the previous pace threshold, as indicated by the deassertion of the Previous Pace Threshold signal. The state machine then waits for the minimum-time timer to expire as indicated by the assertion of MinTime, and for the Previous Pace Threshold signal to be reasserted. This indicates detection of a pulse having sufficient energy, and occurring after a long enough interval from the first pulse, to be regarded as possibly due to the falling edge of a pacing pulse according to the detection algorithm. The machine then moves to the FALLING state. If the Random Noise Threshold and Previous Pace Threshold signals are deasserted, the detected pulse is regarded as noise, and the machine moves back to the WAIT FOR FALLING EDGE state. If the Random Noise Threshold, Previous Pace Threshold, and Fixed Threshold signals are simultaneously asserted, however, the machine transitions to the FALLEN state indicating that a falling edge has possibly been detected. Expiration of the maximum-timer during the WAIT FOR FALLING EDGE, FALLING, or FALLEN states (as indicated by assertion of the MaxTime signal) causes a transition to the TIMEOUT state, which then goes back to the DELAY state. Deassertion of the Random Noise Threshold and Previous Pace Threshold signals causes the machine to move from the FALLEN state to the DETECTED state. From there, if the MaxTime is still not asserted, the machine moves to the VALID EDGE PAIR state and determines whether there is low-frequency energy in the input signal. After expiration of maximum-time RC timer, as indicated by assertion of MaxTime, the state machine checks the low-frequency filtered input to determine whether there has been a low-frequency peak since the start of the timers, as indicated by assertion of LowFreqPresence, which is a latched signal. If the LowFreqPresence signal is non-asserted, the machine transitions to the INVALID state and back to DELAY, discarding the detected edges with generating a valid pace indication. If there has been a low frequency peak, the state machine transitions to the VALID PACE state and asserts the Valid Pace signal. The machine also then asserts the Save Peak signal to move the peak value stored in peak detector PD1 into peak detector PD2 and thereby reset the previous pace threshold. Finally, a transition is made back to the DELAY state where the cycle begins again.

The invention may also be practiced using alternative design techniques. For example, the ECG signal may be sampled a high rate of approximately 60–100 KHz, with the filtering and detection algorithms implemented in the digital domain. Similarly, the pulse width may be measured by digitally determining the time between the rising and falling edges. With the declining cost and faster speed of DSPs, this option may be advantageous, as it would reduce circuit component number, size, and cost, and simplify design development. In another embodiment, separate fixed threshold references for the low-frequency and high-frequency detection bands are employed. Similarly, separate thresholds to detect the rising and falling edges of the pacing signal could be used, which could aid noise rejection because the falling edge magnitude is normally less than the rising edge magnitude. In another variation, a non-linear gain or automatic gain stage is added to the analog input stage to allow a greater dynamic range.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for detecting pacing pulses within an ECG input signal, comprising a high-frequency bandpass filter for filtering the input signal into a high-frequency component representing the energy of the input signal within a high-frequency band;

a low frequency bandpass filter for filtering the input signal into a low-frequency component representing the energy of the input signal within a low-frequency band;

pulse detection circuitry for detecting high and low-frequency energy pulses within the high and low-frequency components, respectively, of the input signal;

a timer for measuring one or more time intervals between detections of the high and low-frequency energy pulses; and, logic circuitry for detecting a pacing pulse within the input signal if the detections of the high and low-frequency energy pulses meet specified timing criteria.

2. The system of claim 1 wherein the pulse detection circuitry detects energy pulses by comparing the high and low-frequency components of the input signal to a threshold value.

3. The system of claim 2 wherein the pulse detection circuitry detects energy pulses by comparing the high and low-frequency components of the input signal to a fixed threshold value.

4. The system of claim 2, wherein the pulse detection circuitry senses an RMS level in the input signal and detects energy pulses in the high-frequency band by further comparing the high-frequency component of the input signal to a threshold value derived from the sensed RMS level in the input signal.

5. The system of claim 2, further comprising a peak measurement circuit for further measuring peak amplitude of the high frequency energy pulses and wherein the pulse detection circuitry detects energy pulses in the high-frequency band by further comparing the high-frequency component of the input signal to a threshold value proportional to the peak amplitude of a previously detected high-frequency energy pulse.

6. The system of claim 5 wherein the threshold value is proportional to the peak amplitude of a previously detected high-frequency energy pulse that was part of a detected pacing pulse.

7. The system of claim 6 wherein the threshold value based upon a prior detection of a high-frequency energy pulse is updated by the logic circuitry when a pacing pulse is detected.

8. The system of claim 1 wherein the logic circuitry detects possible rising and falling edges of a pacing pulse when first and second high-frequency energy pulses are detected by the pulse detection circuitry, and further wherein the timing criteria for detection of a pacing pulse includes detection of the second high-frequency energy pulse within a specified minimum time interval from the detection of the first high-frequency energy pulse.

9. The system of claim 8 wherein the specified minimum time interval is approximately 0.1 milliseconds.

10. The system of claim 8 wherein the timing criteria for detecting a pacing pulse includes detection of a low-frequency energy pulse within a specified time interval with respect to detection of a high-frequency energy pulse.

11. The system of claim 8 wherein the timing criteria for detection of a pacing pulse includes detection of the second high-frequency energy pulse within a specified maximum time interval from detection of the first high-frequency energy pulse.

12. The system of claim 11 wherein the specified maximum time interval is approximately 2 milliseconds.

13. The system of claim 1 wherein the high and low-frequency bandpass filters have center frequencies of approximately 1 KHz and 30 KHz.

14. The system of claim 1 further comprising;

a peak measurement circuit for further measuring peak amplitude of the high frequency energy pulses;

wherein the pulse detection circuitry senses an RMS level in the input signal and detects energy pulses in the high-frequency band if the high-frequency component of the input signal exceeds a fixed threshold value, a threshold value derived from the sensed RMS level in the input signal, and a threshold value proportional to the peak amplitude of a previously detected high-frequency energy pulse which was part of a detected pacing pulse; and, wherein the pulse detection circuitry detects an energy pulse in the low-frequency band if the low-frequency component of the input signal exceeds the fixed threshold value.

15. The system of claim 14 wherein the logic circuitry detects possible rising and falling edges of a pacing pulse when first and second high-frequency energy pulses are detected by the pulse detection circuitry, and further wherein the timing criteria for detection of a pacing pulse includes detection of the second high-frequency energy pulse within specified minimum and maximum time intervals from the detection of the first high-frequency energy pulse.

16. The system of claim 15 wherein the timing criteria for detecting a pacing pulse includes detection of a low-frequency energy pulse within a specified time interval with respect to detection of a high-frequency energy pulse.

17. The system of claim 14 wherein threshold value proportional to the peak amplitude of a previously detected high-frequency energy pulse which was part of a detected pacing pulse is updated with each detected pacing pulse.

18. The system of claim 14 wherein the logic circuitry detects possible rising and falling edges of a pacing pulse when first and second high-frequency energy pulses are detected by the pulse detection circuitry, and further wherein the timing criteria for detection of a pacing pulse includes detection of the second high-frequency energy pulse within a specified minimum time interval from the detection of the first high-frequency energy pulse.

19. The system of claim 18 wherein the logic circuitry is implemented as a state machine which transitions to different states based upon lapsed time intervals and which of the thresholds are exceeded by the low-frequency and high-frequency components of the input signal at a particular time.

20. The system of claim 14 wherein the peak measurement circuit includes a sample-and-hold circuit made up of first and second peak detectors which capacitively store a peak voltage presented to their inputs, wherein the first peak detector stores the peak amplitude of each detected energy pulse which then is transferred to the second peak detector if the energy pulse is deemed part of a pacing pulse.

* * * * *